United States Patent [19]
Ahrens

[11] Patent Number: 5,374,235
[45] Date of Patent: Dec. 20, 1994

[54] MARROW NAIL

[75] Inventor: Uwe Ahrens, Berlin, Germany

[73] Assignee: AAP Gmbh & Co. Betriebs KG, Berlin, Germany

[21] Appl. No.: 46,790

[22] Filed: Apr. 12, 1993

[30] Foreign Application Priority Data

Apr. 10, 1992 [DE] Germany ............... 9205200[U]
Oct. 27, 1992 [DE] Germany ............... 9214970[U]

[51] Int. Cl.⁵ .................................. A61F 5/04
[52] U.S. Cl. ........................ 606/101; 606/62; 606/64; 606/66
[58] Field of Search ............... 606/62, 63, 64, 65, 606/66, 67, 68, 101

[56] References Cited

U.S. PATENT DOCUMENTS

| 3,459,180 | 9/1965 | Ross | 606/67 |
| 5,034,013 | 7/1991 | Kyle et al. | 606/63 |
| 5,041,115 | 8/1991 | Frigg et al. | 606/67 |
| 5,102,413 | 4/1992 | Poddar | 606/62 |

Primary Examiner—Stephen C. Pellegrino
Assistant Examiner—Sonya C. Harris
Attorney, Agent, or Firm—Cohen, Pontani, Lieberman, Pavane

[57] ABSTRACT

A marrow nail engagable with a plurality of screws for securing the nail in a bone of a patient. The marrow nail includes a plurality of recesses defined proximate one end of an elongated rod. Each of the plural recesses is formed as a notch and is operably engagable with a respective one of the plural screws. A holding arrangement is disposed at the other end of the marrow nail rod and is implemented as a threaded assembly for facilitating movement of the marrow nail in the patient.

15 Claims, 3 Drawing Sheets

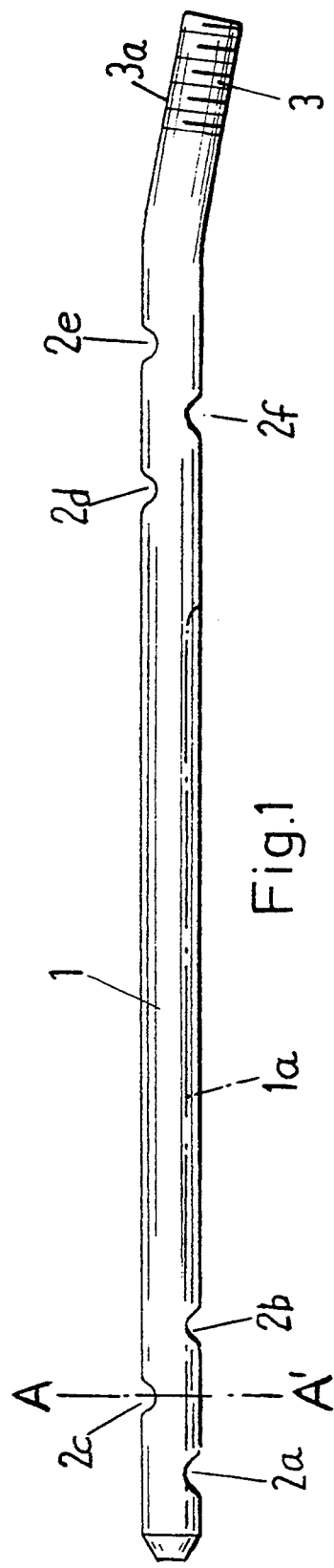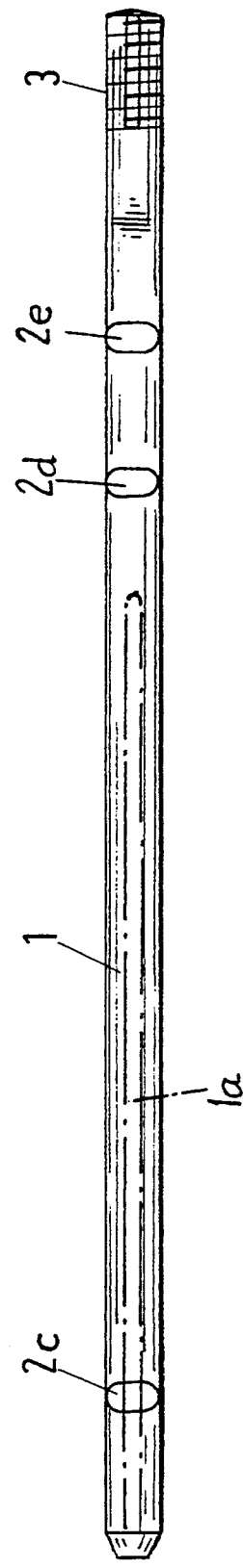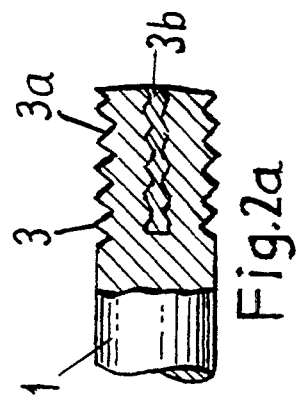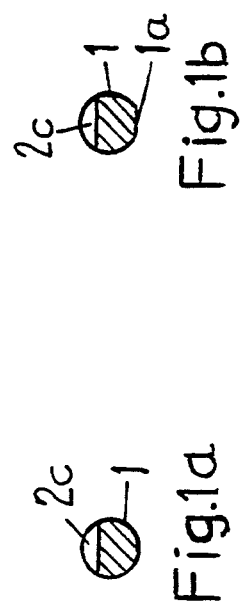

MARROW NAIL

FIELD OF THE INVENTION

The present invention is directed to a marrow nail, in particular to a marrow nail whose one end is provided with a plurality of recesses which, in cooperation with screws, enable the marrow nail to be secured in a bone. The present invention is also directed to a marrow nail having a holding arrangement at the opposite, proximal end thereof.

BACKGROUND OF THE INVENTION

Marrow nails are used in tubular bones in humans and animals for healing fractures or for facilitating bone elongation. In marrow nails known in the prior art, the nails are secured in the bone by screws which must be guided through bore holes provided in the marrow nail. In these known marrow nails, an elongated hole is provided at the opposite, proximal end of each of the nails which elongated hole may be used in cooperation with a hook for outward movement or deflection of the nail. However, such marrow nails have several disadvantages. For example, problems are caused on the one hand by the necessity of guiding the screws through the bore holes in the nail. This arrangement renders it difficult to secure the screws to the marrow nail. In addition, the connection of the marrow nail with the hook is cumbersome and inconvenient.

OBJECT OF THE INVENTION

The object of the present invention is to provide a marrow nail which is considerably simpler to handle and use and has improved strength and securement characteristics.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

SUMMARY OF THE INVENTION

According to one aspect of the present invention, a marrow nail is provided with notches arranged on opposite sides of the nail, instead of bore holes as conventionally known, so that the cooperating screws need only be inserted in these notches when securing the nail in the bone. Moreover, the notches are formed having rounded edges which result in substantial optimization of tension and significantly improves the strength of the nail for securing the marrow nail in the bone. Further, the marrow nail includes a threaded assembly at the proximal end for providing additional security and reliability when removing the nail. This feature notably simplifies use as compared with a conventional nail.

According to a further aspect of the present invention, the notches are constructed in such a way that there is a positive or frictional locking connection with the cooperating screws to secure the nail in the bone. In particular, this connection may be implemented by arranging adjacent notches radially or circumferentially offset from one another with respect to the longitudinal axis of the nail. As such, the notches may be so arranged that, when the screws are inserted in these notches, the screws form together with the nail either, by way of example, a triangular shape or an open rectangular shape.

According to another aspect of the present invention, the notches are each provided with a threaded assembly for engagement with the threads of corresponding screws. Finally, the notches may also include, at their upper edge, undercuts which partially enclose the screw surface. These features prevent lateral slipping of the marrow nail in the epiphyses of the bone.

As is well known to those of ordinary skill in the art, the marrow space of the tubular bone has its smallest diameter in the central region of the bone, known as the diaphysis region. This is an important factor in selecting a marrow nail to be secured in the bone without drilling in the marrow space. Additionally, the marrow space becomes larger toward the epiphyses, i.e. toward the ends of the bone. In accordance with the present invention, the positive or frictional locking connection between the nail and the screws prevents displacement of the nail in the vertical plane. Stability against tilting is readily achieved solely by the use of as few as two screws at the nail, since each screw represents a possible center of rotation in a direction and tilting is accordingly prevented in the sagittal plane.

DETAILED DESCRIPTION OF THE DRAWINGS

In the drawings, wherein like reference characters denote similar elements throughout the several views:

FIG. 1 is a side view of a marrow nail according to the present invention;

FIG. 1a is a cross-sectional view of the marrow nail taken along line A—A' of FIG. 1;

FIG. 1b is a cross-sectional view of another aspect of the marrow nail taken along line A—A' of FIG. 1;

FIG. 2 is a top view of the marrow nail of FIG. 1;

Figures 3, 3A, 3B:
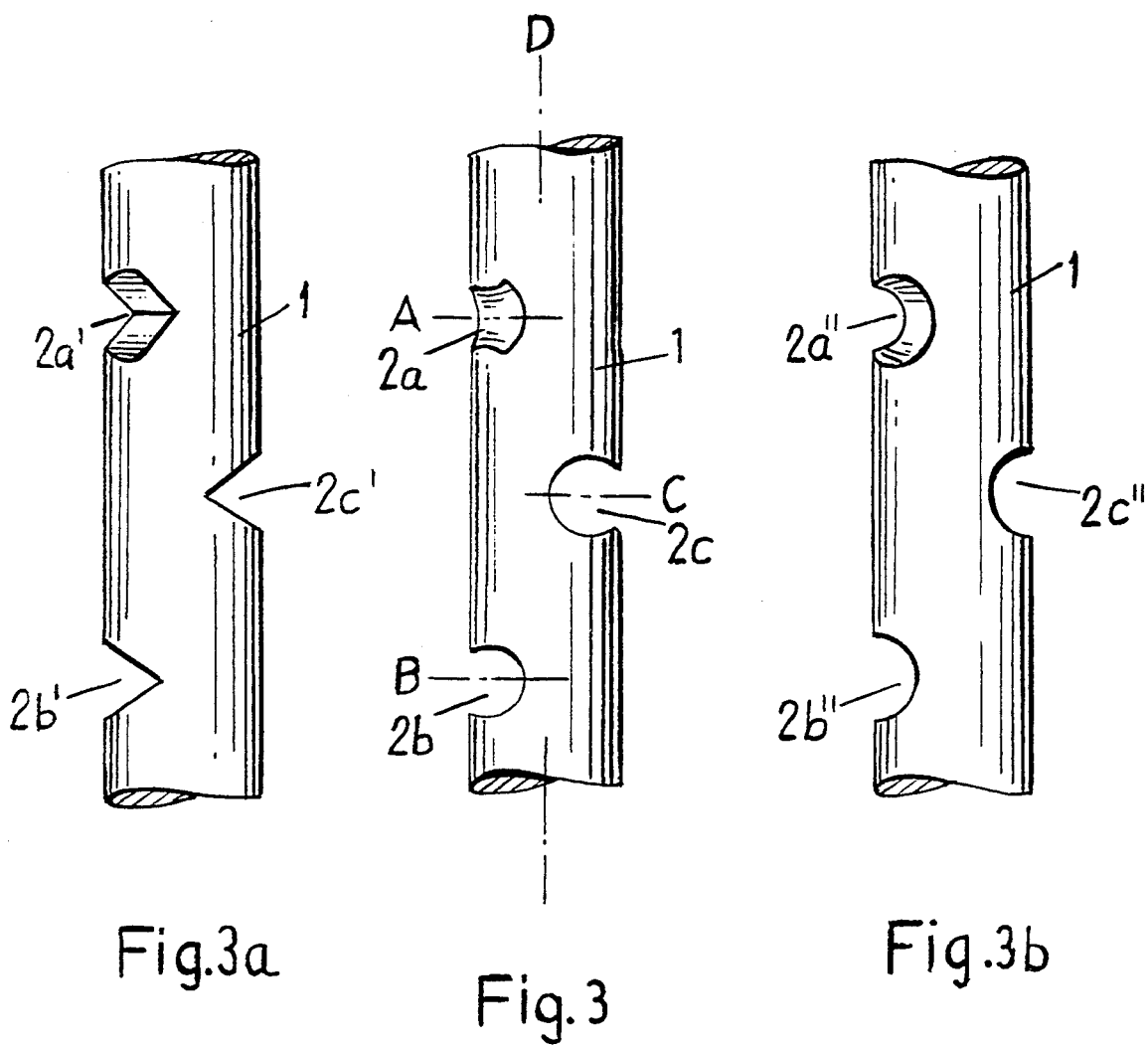
Figure 4:
Figure 5:
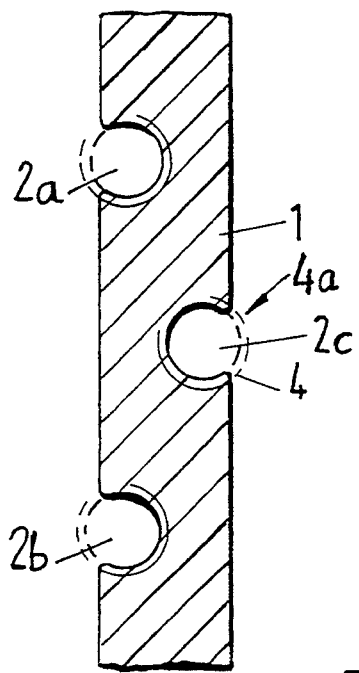
Figure 5A:
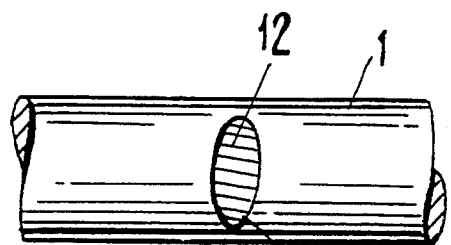
Figure 6:
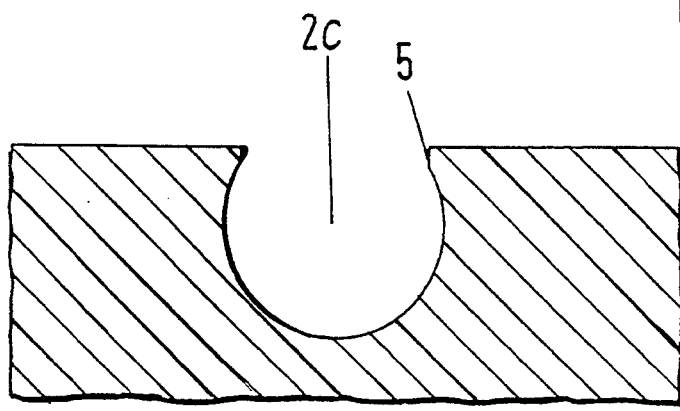
Figure 7:
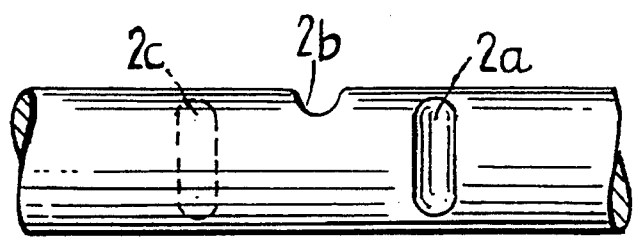

FIG. 2a discloses an enlarged view of a portion of the marrow nail of FIG. 2;

FIG. 3 is an enlarged, partial side view of a marrow nail constructed in accordance with another aspect of the invention;

FIG. 3a is an enlarged, partial side view of a marrow nail constructed in accordance with a further aspect of the invention;

FIG. 3b is an enlarged, partial side view of a marrow nail constructed in accordance with yet another aspect of the invention;

FIG. 4 is a cross-sectional view of a notch formed in the inventive marrow nail;

FIG. 5 is a cross-sectional view of the marrow nail of FIG. 3 taken along its longitudinal axis;

FIG. 5a is a perspective view of the marrow nail of FIG. 5;

FIG. 6 is a detailed cross-sectional view of a marrow nail region including notch 2-c of FIG. 3; and FIG. 7 is a perspective view of another embodiment of the marrow nail of the present invention having 90° offset notches.

DETAILED DESCRIPTION OF THE PRESENTLY PREFERRED EMBODIMENTS

Referring to FIG. 1, marrow nail 1 in the general form of an elongated rod or shaft includes a plurality of recesses or notches 2-a to 2-f formed and defined therein at various positions along the length of the nail. Notches 2-a, 2-b and 2-c having smoothly rounded edges are provided at a distal end of the marrow nail 1. Preferably and as best seen in FIG. 1a, which is a cross-sectional view of FIG. 1 along the lines A—A', notch 2-a has a generally secant-like cross-section. In the present example, notches 2-a and 2-b are provided on one side and notch 2-c is provided on the opposite side or, in other words, at a 180° circumferential offset to the notches 2-a and 2-b. Similarly, notches 2-d, 2-e and 2-f are provided at the opposite or proximal end of the nail as seen in the figure. Notches 2-a through 2-f have a generally circular cross-sectional shape as shown in FIG. 3. Of course, as will be understood by one of ordinary skill in the art, notches having other cross-sectional shapes may also be employed. For example, FIG. 3a illustrates notches 2-a' through 2-c' having a triangular cross-section and FIG. 3b illustrates notches 2-a" through 2-c" having a semicircular cross-section.

FIG. 1 illustrates a nail having six notches although, as will be apparent to those of ordinary skill in the art who have read this description, more or fewer notches may alternatively be employed. As depicted in FIG. 1, the arrangement of the oppositely-located notches prevents torsional twisting of the marrow nail 1. Additionally, bore holes (not shown) may be defined in the nail for providing further protection against torsional twisting. FIG. 1b is a cross-sectional view taken along the lines A—A' of FIG. 1 and depicts another aspect of the preferred embodiment in which the marrow nail may also be flattened at one side to form a flattened edge 1a extending along at least a portion of its axial length; this arrangement may be utilized to prevent the destruction of blood vessels which supply blood to the bone. As shown by FIG. 2a, a threaded portion or assembly 3 is provided at the proximal end of the nail 1 and is preferably constructed having internal 3b and external 3a threads so that either or both threads can be used for outward movement or deflection of the marrow nail by a user, e.g. surgeon, exerting a force.

According to the present invention, the cooperating screws need merely be inserted into the notches 2-a through 2-f when securing the marrow nail to the bone, instead of the need to carefully engage such screws with the bore holes of conventional marrow nails. This arrangement overcomes the aforementioned disadvantages in heretofore known marrow nails. More particularly, a marrow nail constructed according to the present invention is simpler and more convenient to use.

FIGS. 3–6 show details of construction according to another preferred embodiment. The notches 2-a to 2-f are arranged on the marrow nail so as to provide a frictional locking means to secure the cooperating screws to the marrow nail 1. As illustrated in FIGS. 3 and 4, this is accomplished by positioning the notches such that their respective longitudinal axes, designated by lines A, B and C, are radially or circumferentially offset from one another with respect to the longitudinal axis D of the marrow nail. When the notches are arranged as 120° apart, the screws inserted into these notches form with the nail a triangular shape. Alternately, when notches 2-a through 2-c are arranged 90° apart, the screws inserted therein form with the nail an open rectangular shape as shown by FIG. 7. As should be readily apparent, by arranging the notches 2a–2c in this fashion twisting of the marrow nail 1 can be prevented.

As shown in FIG. 5, a threaded configuration or assembly 4a is formed in the notches 2a–2c. In this arrangement, cooperating screws 4 are threadably engaged with the threaded notches 2c, having threads 12 of the marrow nail 1 to secure the marrow nail 1 in the bone.

FIG. 6 is a partial cross-sectional enlarged view showing one of the notches of the embodiment of FIG. 3. As seen in the figure, the notches have undercuts 5 which enclose or capture the screws along at least a portion of their circumference. This arrangement enables the screw to be easily inserted into the notch to secure the nail 1 to the bone.

While there have been shown and described and pointed out fundamental novel features of the invention as applied to preferred embodiments thereof, it will be understood that various omissions and substitutions and changes in the form and details of the disclosed apparatus may be made by those skilled in the art without departing from the spirit of the invention. It is the intention, therefore, to be limited only as indicated by the scope of the claims appended hereto.

What is claimed is:

1. A marrow nail engageable with a plurality of screws for securing the marrow nail in a bone of a patient, said marrow nail comprising:
   an elongated rod having an outer periphery extending along a longitudinal axis, and including two longitudinally spaced end portions;
   a plurality of notches defined proximate one of said end portions of said rod and that open onto said outer periphery for operative engagement with a corresponding plurality of cooperating screws that extend substantially tangentially to the outer periphery of the marrow nail for securing the marrow nail in the bone, each said notch being configured for receiving only a part of a cross-section of a respective one of said screws, said notches defining a continuous surface and solid material of said rod being between and beneath said notches; and
   the other end of said end portions of said rod comprising a threaded assembly for facilitating movement of said marrow nail in the patient.

2. A marrow nail according to claim 1, wherein adjacent ones of said plurality of notches are defined in opposite transverse sides of said rod.

3. A marrow nail according to claim 1, wherein each of said notches has a secant-like shape.

4. A marrow nail according to claim 1, wherein said plurality of notches are arranged in a V-shaped manner.

5. A marrow nail according to claim 1, wherein each of said plural notches has a semicircular cross-sectional shape.

6. A marrow nail according to claim 5, wherein each of said plural notches has a rounded edge.

7. A marrow nail, a marrow nail engageable with a plurality of screws for securing the marrow nail in a bone of a patient, said marrow nail comprising:
   an elongated rod having an outer periphery extending along a longitudinal axis, and including two longitudinally spaced end portions;
   a plurality of notches defined proximate one of said end portions of said rod and that open onto said outer periphery for operative engagement with a corresponding plurality of cooperating screws that extend substantially tangentially to the outer periphery of the marrow nail for securing the marrow nail in the bone, each said notch being configured for receiving only a part of a cross-section of a respective one of said screws; and
   means for holding the other of said end portions of said rod comprising a threaded assembly for facilitating movement of said marrow nail in the patient, wherein said threaded assembly comprises internal and external threads at said other end of said rod.

8. A marrow nail, engageable with a plurality of screws for securing the marrow nail ill a bone of a patient, said marrow nail comprising:

an elongated rod having an outer periphery extending along a longitudinal axis, and including two longitudinally spaced end portions;

a plurality of notches defined proximate one of said end portions of said rod and that open onto said outer periphery for operative engagement with a corresponding plurality of cooperating screws that extend substantially tangentially to the outer periphery of the marrow nail for securing the marrow nail in tile bone, each said notch being configured for receiving only apart of a cross-section of a respective one of said screws; and means the holding the other of said end portions of said rod comprising a threaded assembly for facilitating movement of said marrow nail in tile patient, further comprising a flattened edge extending longitudinally along said marrow nail.

9. A marrow nail according to claim 1, wherein said plurality of notches are defined at circumferential positions about said rod so as to provide a frictional engagement of said plural notches with a corresponding plurality of the cooperating screws.

10. A marrow nail according to claim 9, wherein said plural notches are axially distributed along said rod, and wherein axially adjacent ones of said plural notches are circumferentially offset from one another with respect to the longitudinal axis of said rod.

11. A marrow nail according to claim 10, wherein said plurality of notches are arranged such that when the plurality of screws are inserted into said plurality of notches, the plurality of screws and said rod form one of a triangular shape and an open rectangular shape.

12. A marrow nail according to claim 10, wherein said plural notches are circumferentially offset at angles of approximately 120° about the circumference of said rod.

13. A marrow nail according to claim 10, wherein said plural notches are circumferentially offset at angles of approximately 90° about the circumference of said rod.

14. A marrow nail according to claim 9, wherein each of said plural notches comprises a threaded assembly for threaded engagement with a corresponding one of the plural screws.

15. A marrow nail according to claim 9, wherein each of said plural notches comprises an undercut formed along an upper edge of the notch for partially capturing a surface of a corresponding one of the plural screws when the screw is inserted into a bone for securing said marrow nail in the bone.

* * * * *